United States Patent [19]
Paulson et al.

[11] Patent Number: 6,105,177
[45] Date of Patent: Aug. 22, 2000

[54] PROTECTIVE GOGGLES

[75] Inventors: Roy V. Paulson, Temecula; Donald R. Reiterman, Hemet; Richard B. Christner, Lake Elsinore, all of Calif.

[73] Assignee: Paulson Manufacturing Corp., Temecula, Calif.

[21] Appl. No.: 08/998,517

[22] Filed: Dec. 26, 1997

[51] Int. Cl.⁷ ........................................................ A61F 9/02
[52] U.S. Cl. .................... 2/431; 2/436; 2/441; 2/452; 2/444
[58] Field of Search ................................ 2/426, 428, 430, 2/431, 436, 437, 439, 440, 441, 447, 452, 454; 351/47, 62, 44, 157; 359/159, 168, 169, 164, 171

[56] References Cited

U.S. PATENT DOCUMENTS

| | | | |
|---|---|---|---|
| 4,743,105 | 5/1988 | Tabacchi | 351/157 X |
| 5,410,763 | 5/1995 | Bolle | 2/444 X |

OTHER PUBLICATIONS

Encon Eye Protection, 500 Series Goggle, 2 pages (1989).
Encon Eye Protection, 160 Series Goggle, 2 pages (1989).
U.S. Safety, The Legend, 2 pages (1993).

*Primary Examiner*—Peter Nerbun
*Attorney, Agent, or Firm*—Baker & Maxham

[57] ABSTRACT

Goggles for protecting the eyes of a wearer in ultra-hazardous conditions. The goggles comprise a frame that seals to the face of the wearer so that the wearer's eyes are enveloped. An adjustable strap is attached to the goggles and goes around the head of the wearer in order to secure the goggles over the wearer's face. Indirect ventilation is utilized to eliminate fogging, and drains are used in the frame to evacuate trapped moisture. A curvilinear lens with multiple optical zones is secured within the frame of the goggles and angled for increased lower peripheral vision. The materials with which the goggles are constructed are capable of withstanding a temperature of at least about 550° F. for a minimum of five minutes without oozing or dripping or otherwise deforming.

47 Claims, 10 Drawing Sheets

PROTECTIVE GOGGLES

BACKGROUND OF THE INVENTION

1. Field of the Invention

This invention relates generally to protective eye wear and more particularly, for example, to goggles that protect the eyes of a firefighter from ultra-hazardous conditions.

2. Discussion of the Prior Art

When it is necessary to work in high temperature hazardous conditions such as those encountered by a firefighters precautions to protect the firefighter's eyes become a necessity. Many different designs for eye protection under such severe high temperature conditions have been proposed. The eye protection previously known generally seeks to protect an individuals entire face against the hazardous conditions by using a heat-resistant face shield.

Little attention has been given to specifically protecting a user's eyes from high temperature hazardous conditions by using a pair of goggles. To date, no goggles exist which are designed for the purpose of meeting these high temperature hazardous conditions. This is important because goggles, as opposed to a face shield, are quicker and easier to use, can easily be adapted for use with a filter or respirator device, and provide enhanced eye protection. For the foregoing reasons, there is a need, especially for firefighters, for goggles that offer superior eye protection, overcome the shortcomings of currently available goggles, and enhance visibility.

SUMMARY OF THE INVENTION

Broadly speaking, the present invention is directed to an apparatus that satisfies the need for high temperature-resistant goggles that protect the wearer's eyes from ultra hazardous conditions, including extremely high temperatures and foreign materials which might otherwise impair the wearer's vision.

The goggles of this invention primarily comprise an assembly of four main elements: a frame, a lens, a bezel, and a strap. The frame is used in conjunction with the bezel and the lens to protect the eyes of the wearer, and the strap is used to secure the goggles in place. These goggles are: designed to form a comfortable fit and seal against the wearer's nose and face; configured to prevent moisture from accumulating on the inside of the goggles; configured to prevent foreign materials from entering from outside the goggles, and; designed to allow the goggles wearer to easily fit the goggles to his face while easily accommodating spectacles, when necessary, normally worn close to the user's face. The unique frame design allows the goggles to collapse flat, with the exception of the lens, for easy storage in a small space, such as a pocket, when not in use.

In one embodiment, the lens used in the goggles is curved and provides multiple optical zones integral therewith for enhanced undistorted vision. The frame securely holds the lens in place over the wearer's eyes. A bezel is attached to the frame. Opening covers are coupled to the bezel and cooperate with dams formed around the openings in order to prevent water or other undesirable matter from entering the interior of the goggles when they are on the wearer's face. The bezel includes an attachment which cooperates with the strap to adjustably secure the goggles in place on the wearer's face.

BRIEF DESCRIPTION OF THE DRAWING

The objects, features, and advantages of the present invention will become better understood with regard to the following description and appended claims, when read in conjunction with the accompanying drawing, wherein:

DETAILED DESCRIPTION OF THE PREFERRED EMBODIMENTS

Figure 1:
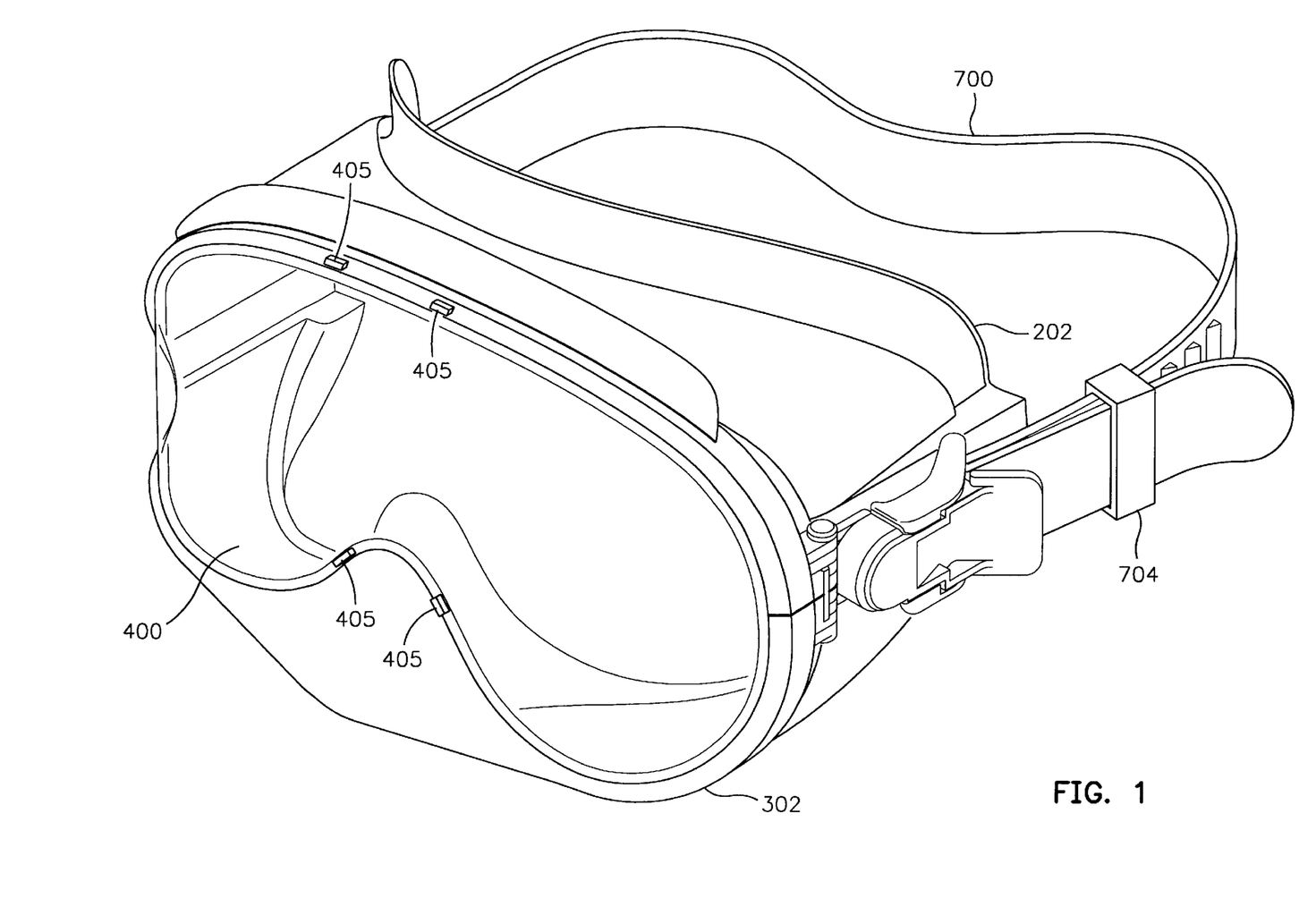
FIG. 1 is a perspective view of goggles constructed in accordance with one embodiment of the present invention.

With reference now to the drawing, and more particularly to FIG. 1 thereof, there is shown a perspective view of a preferred embodiment of the assembled goggles of the present invention. Generally, the goggles fit completely over the eyes and surrounding facial area of the wearer and a strap is placed around the wearer's head or safety hat to secure the goggles to the wearer's face. The goggles shown in FIG. 1 utilize a flexible frame 202 which is used to disconnectably house a curvilinear lens 400. A semi-rigid bezel 302 is removably affixed to the flexible frame 202. A strap 700 is coupled to the bezel, allowing the goggles to be removably and adjustably secured to the face of the wearer when the strap is passed around the back side of the wearer's head. A strap retainer means 704 is used in conjunction with the strap in order to retain any loose ends of the strap.

In one embodiment, the frame 202, shown in detail in FIGS. 2A through 2D, has six sides integral thereto: a lens side 206 opposite to a flange side 204; an upper side 208 opposite to a lower side 222; and a first strap end 212 opposite to a second strap end 214. The frame 202 is made of a flexible material to allow the frame to be comfortably fitted to the face of the wearer, and to allow the frame to be selectively, substantially collapsed for storage.

Figure 2A:
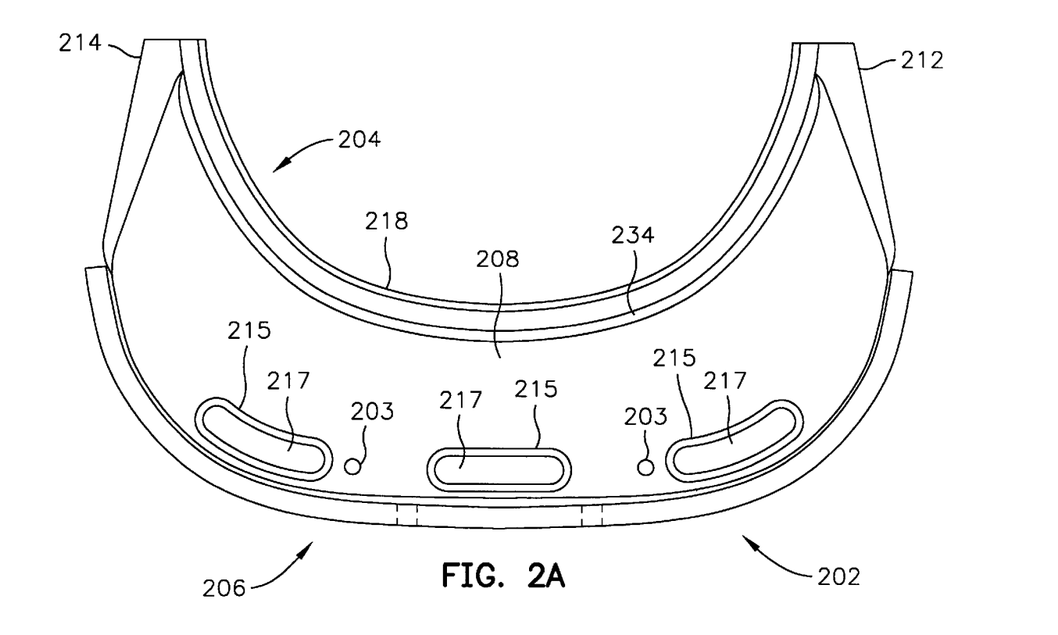
FIG. 2A depicts a plan view of the frame of the goggles of FIG. 1 as viewed from above.
Figure 2B:
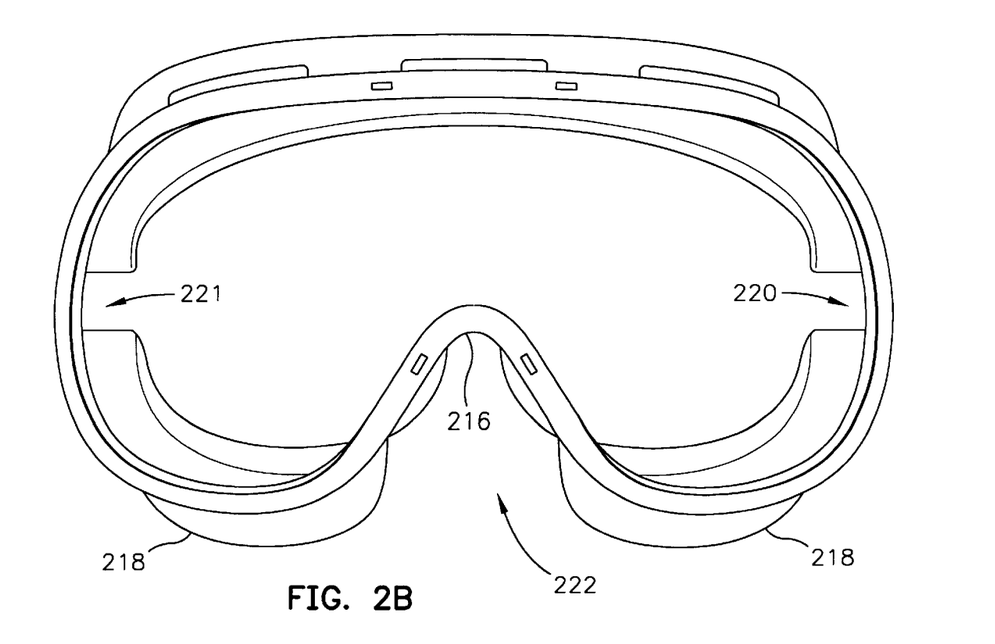
FIG. 2B shows a lens-side view of the frame of the goggles of FIG. 1.
Figure 2C:
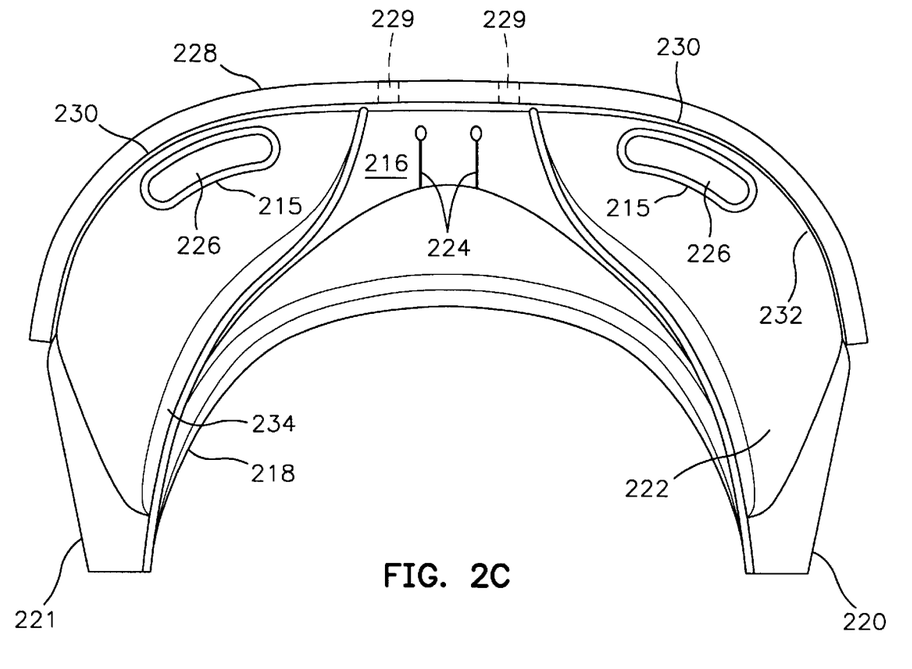
FIG. 2C illustrates a plan view of the frame of the goggles of FIG. 1 as viewed from below.

The lens side 206 of the frame 202 incorporates a lens surround area 228 as shown in FIG. 2C. The lens surround area incorporates lens surround slots 229 through which lens tabs 405, discussed below, extend. The tabs and a lens retention channel 230 capture the lens 400 by its perimeter 406 (shown in FIGS. 4A and 4B) and secures the lens to the frame 202. However, the lens could also be secured to the lens surround area 228 by other suitable means such as snaps, adhesives, or by molding the lens directly into the frame.

Figure 2D:
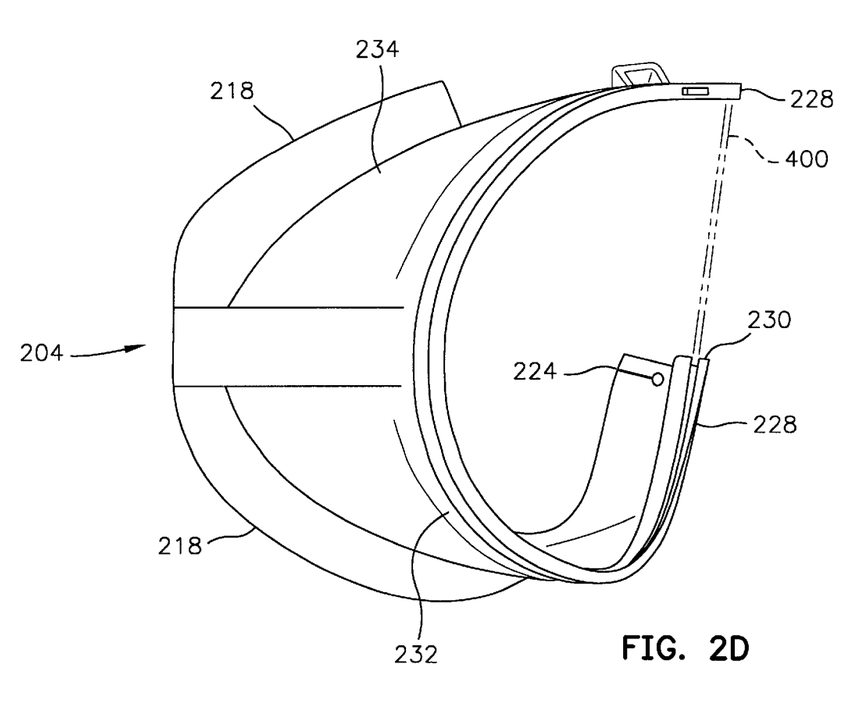
FIG. 2D is a plan view of a first strap end of the frame of the goggles of FIG. 1.

Located opposite to the lens side 206 is the flange side 204 as shown in FIG. 2D. A face flange 218 is integrated with the flange side 204 in order to assure proper sealing of the goggles to the wearer's face. For cold weather applications, a foam seal (not shown) may be used and secured by adhesive or many types of fasteners, including hook-and-loop snaps or friction, to the face flange 218 to enhance the seal. The lens side 206 and the flange side 204 are separated by the upper side 208 shown in FIG. 2A, the lower side 222 shown in FIG. 2C, the first strap end 212, and the second strap end 214, both shown in FIG. 2A.

In one version of the present invention as shown in FIG. 2C, the lower side 222 of the frame 202 has second openings 226 which are surrounded by dams 215. A nose section 216 (shown in FIG. 2B) is formed in the lower side 222 in order to accommodate the nose of the wearer and to assure that the goggles seal properly atop the wearer's nose. The nose section 216 cooperates with the face flange 218 to complete a proper seal to the wearer's face. At least one nose release 224 is integral to the nose section and allows for a more comfortable fit by allowing greater flex in the nose section while maintaining a tight seal. A first gutter 234 is formed into the frame 202 and is juxtaposed to the face flange 218. The gutter channels liquid and debris that strike the frame away from the face flange.

The upper side 208 as shown in FIG. 2A has first openings 217 in one version of the invention which are surrounded by the same kind of dams 215. A second gutter 232 is integral to the frame and juxtaposed to the lens surround area 228. The upper side 208 is separated from the lower side 222 by the first strap end 212 and the second strap end 214.

Completing the frame in one embodiment are first and second strap ends 212 and 214, respectively, each accommodating a first and second channel 220 and 221, respectively, shown in FIGS. 2B and 2C. As shown in FIGS. 2C and 2D, both channels extend from the second gutter 232 toward the flange side 204, bisecting the first gutter 234 and the face flange 218. In the preferred embodiment, the channels 220 and 221 are designed such that the frame 202 can easily be slid over the eyeglasses of a wearer without the wearer having to remove the eyeglasses before fitting the goggles.

Figures 2E, 3B:
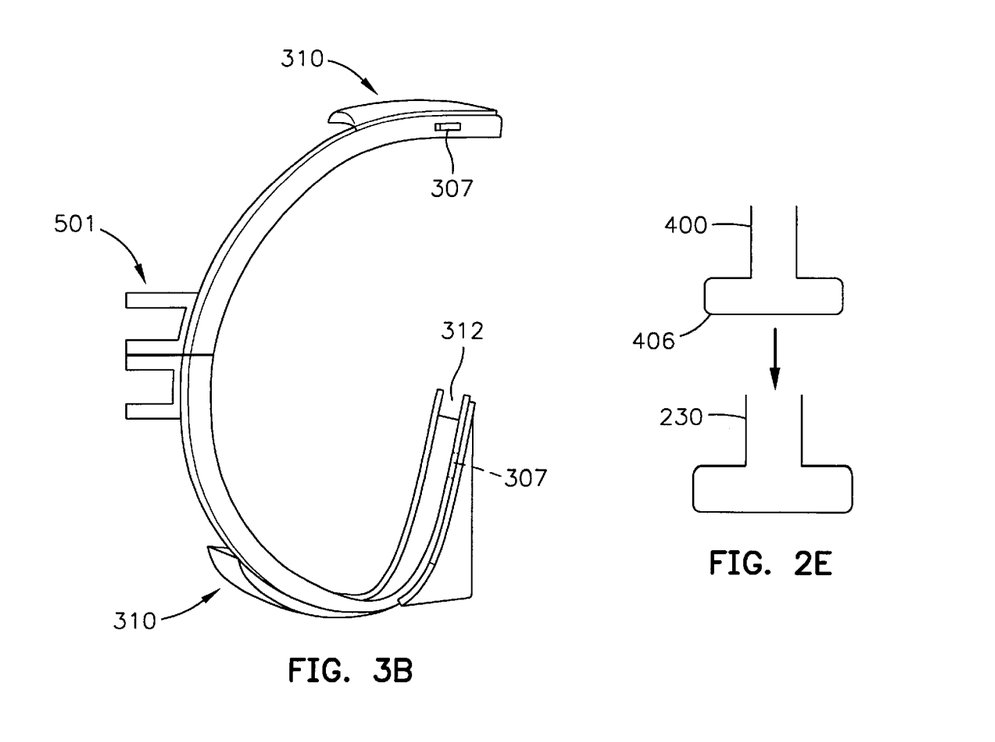
FIG. 2E depicts a T-shaped lens section and a T-shaped goggle frame section.
FIG. 3B is a perspective view of a first strap end of the bezel used with the goggles of FIG. 3A.
Figure 4A:
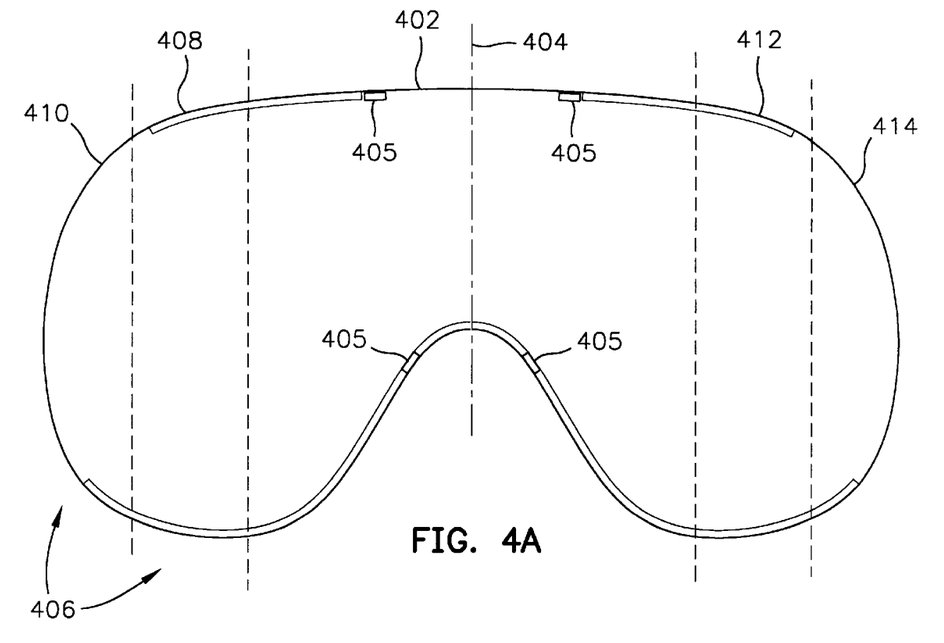
FIG. 4A is a front view of the lens of the goggles of FIG. 1.

As indicated above and as shown in FIG. 2D, the curvilinear lens 400 is captured about its lens perimeter 406 shown in FIG. 4A in one embodiment by the lens retention channel 230. Preferably, the lens perimeter and the lens retention channel are both "T" shaped, thereby allowing the lens perimeter to be securely cradled by the lens retention channel so that the lens 400 will not separate from the frame 202 if impacted. As shown in FIG. 2E, sections of the lens retention channel 230 are T-shaped to slidably receive the T-shape sections of the lens perimeter 406. This "cradling" allows the lens to seal to the frame and prevents any foreign substance from passing between the lens 400 and the frame. Furthermore, the lens perimeter 406 preferably has tabs 405 extending substantially perpendicular therefrom and away from an outer surface 401 of the lens 400, the outer surface and the tabs 405 being shown in FIG. 1. Although four such tabs are shown, several tabs may be spaced around the periphery.

Figure 4B:
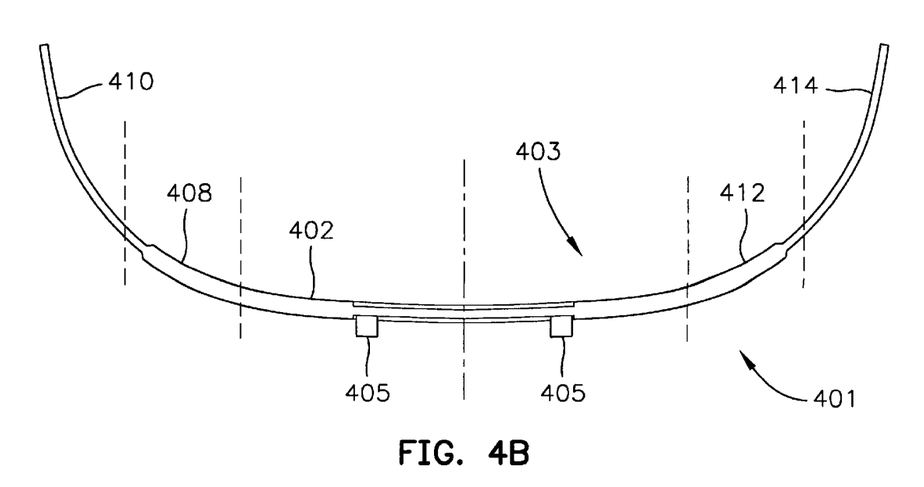
FIG. 4B is a view of the lens of FIG. 4A as viewed from above.

In one version of the invention shown in FIG. 4B, the curvilinear lens 400 has an inner surface 403 and an outer surface 401. The inner surface and the outer surface may be substantially parallel, or may converge or diverge. In a preferred embodiment, the outer surface of the lens diverges with the inner surface so that the thickness of the lens as measured between the inner surface and outer surface is maximized toward the center of the lens. In one embodiment, the distance between the inner and outer surface may vary between approximately 0.08 inch and 0.100 inch. Preferably, the inner surface 403 is treated with an anti-fog substance and the outer surface 401 is treated with an abrasion-resistant substance. The shape of the lens 400 allows a unique shape for the goggles to be achieved, thereby substantially reducing and preferably eliminating distortion between the multiple optical zones of the lens and allowing the goggles to be placed on the face of the wearer without the wearer having to first remove his spectacles which, for goggles wearers with corrected vision, may be a necessity. For example, a firefighter may have to quickly put the goggles on over his glasses while threatened by flames in zero-visibility situations.

Generally, the lens 400 may have five curvilinear optical zones each distinguished by broken lines in FIGS. 4A and 4B. These optical zones comprise: a curvilinear central optical zone 402 on either side of center line 404; a first and a second curvilinear side optical zone 408 and 412, respectively; and a first and a second curvilinear rear optical zone 410 and 414, respectively. The lens 400 extends vertically between the lower side 222 and the upper side 208 of the frame 202, and horizontally between the first and second strap ends 212 and 214. In one embodiment, shown in FIG. 2D, the lens 400 is canted within the frame 202 in order to increase the lower peripheral vision of the wearer and allow the wearer to see the ground immediately before him.

When properly positioned in the frame 202, the central optical zone 402 of lens 400 is substantially centered within the lens surround area 228. As shown in FIGS. 4A and 4B, the first side optical zone 408 is contiguous to the central optical zone 402 and is positioned between the central optical zone and the first rear optical zone 410. Preferably, the two side optical zones 408 and 412 are hyperbolically curved in a direction substantially perpendicular to a vertical centerline 404. The first side optical zone 408 is also contiguous to the first rear optical zone 410. The first rear optical zone is positioned between the first side optical zone 408 and, when mounted in the frame, the first strap end of the frame. The second side optical zone 412 is also contiguous to the central optical zone and is positioned between the central optical zone and the second rear optical zone 414. The second side optical zone is contiguous to the second rear optical zone which is positioned between the second side optical zone and, when mounted in the frame, the second strap end of the frame.

The radius of curvature for each curvilinear zone discussed—at the point of contiguity to the respective abutting zone—is equal to the radius of curvatures of the abutting zone. This equal radius of curvature at the point of contiguity substantially eliminates optical distortion that might otherwise be perceived by the wearer due to the transition from one zone to another. Although the use of only one lens is discussed in conjunction with the preferred embodiment, multiple lenses could be used in an alternative embodiment. Similarly, any number of curvilinear optical zones could be integral to the lens 400.

Figure 3A:
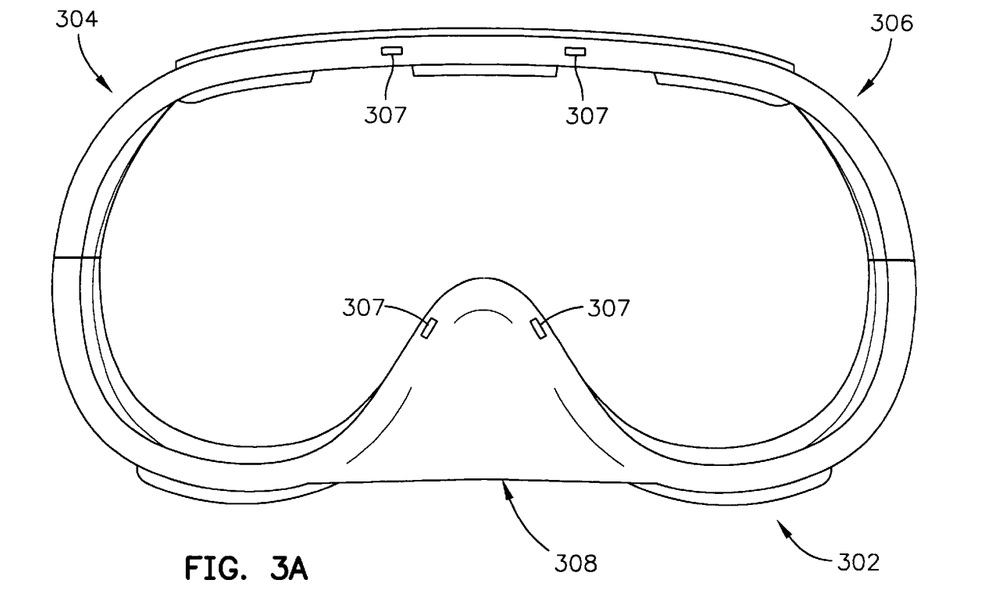
FIG. 3A depicts the front of the bezel of the goggles including a nose guard used in another, and preferred, embodiment of the present invention.
Figure 3C:
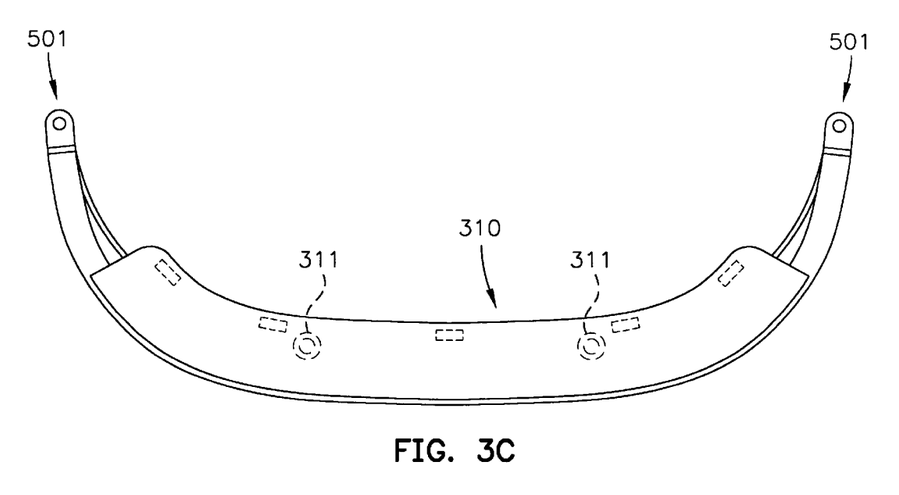
FIG. 3C is a plan view of the bezel of FIG. 3A as viewed from above.
Figure 3D:
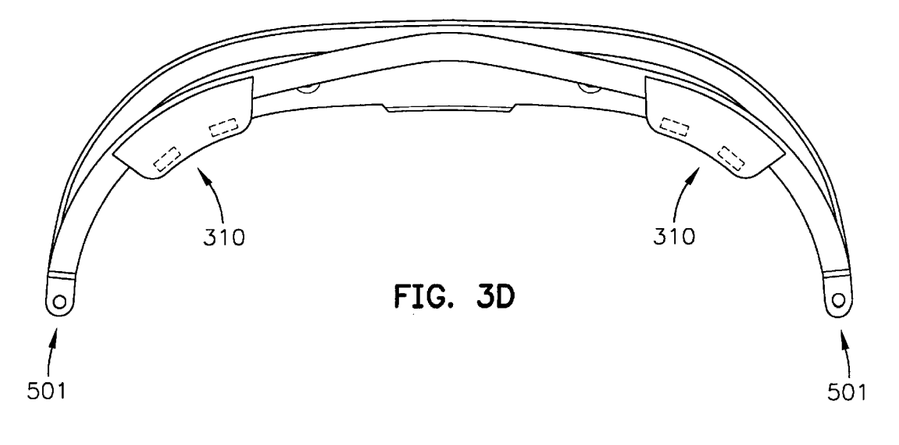
FIG. 3D is a plan view of the bezel of FIG. 3A as viewed from below.

The detail of the bezel 302 of a second embodiment of the invention is shown in FIGS. 3A through 3D. In this embodiment, the bezel 302 is two-piece and semi-rigid, and cooperates with the lens retention channel 230 to further secure the lens 400 in the frame 202. In the preferred embodiment, a bezel attachment channel 312 is formed into the bezel 302 and tightly cradles the lens surround area 228, which includes lens retention channel 230, which in turn tightly cradles the perimeter 406 of the lens 400. Slots 307 are included in the bezel as shown in FIGS. 3A and 3B and engage tabs 405 extending from lens 400. This preferred attachment arrangement allows the bezel 302 to be removably attached to the lens surround area 228 of the frame 202 while preventing separation between the frame and the lens 400. Alternatively, the bezel 302 may be attached to the frame by adhesive, snaps, or molded fitting, for example. The two-pieces of the bezel are coupled together by a bezel clip 504 being slid over a two-piece center projection 503 of a bezel clip receiver as shown in FIG. 5.

The bezel 302 has a first end 304 and a second end 306 that cooperate with the strap 700 (FIG. 7) and an attachment means used to hold the two-piece bezel together and secure the goggles to the face of the wearer. In one embodiment, opening covers 310 having setoff tabs are coupled to the bezel 302 and are positioned in such a way that these opening covers extend over first openings 217 and second openings 226 when the bezel 302 is attached to the frame 202. The set-off tabs keep the openings clear by preventing sealed contact with the opening covers. The opening covers also cooperate with dams 215 which surround the first and second openings 217 and 226, respectively, to prevent foreign matter from contacting the eyes of the wearer. To prevent a gap from opening up between the frame 202 and the opening covers 310 which cover first openings 217, barbed fasteners 311 shown in FIG. 3C and integral to the opening covers 310 button to holes 203 shown in FIG. 2A. This arrangement allows the bezel 302 to be removed from the frame 202 to facilitate replacement of the lens 400, if necessary. Although barbed fasteners 311 are preferred, any detachable fastening arrangement may be used, such as snaps, integral molding, tabs, or the like. Optionally, a nose cover 308 as shown in FIG. 3A can be integrated with the bezel 302 in a position to cover the nose of the wearer when the goggles are positioned over the eyes of the wearer.

Figures 7, 7A:
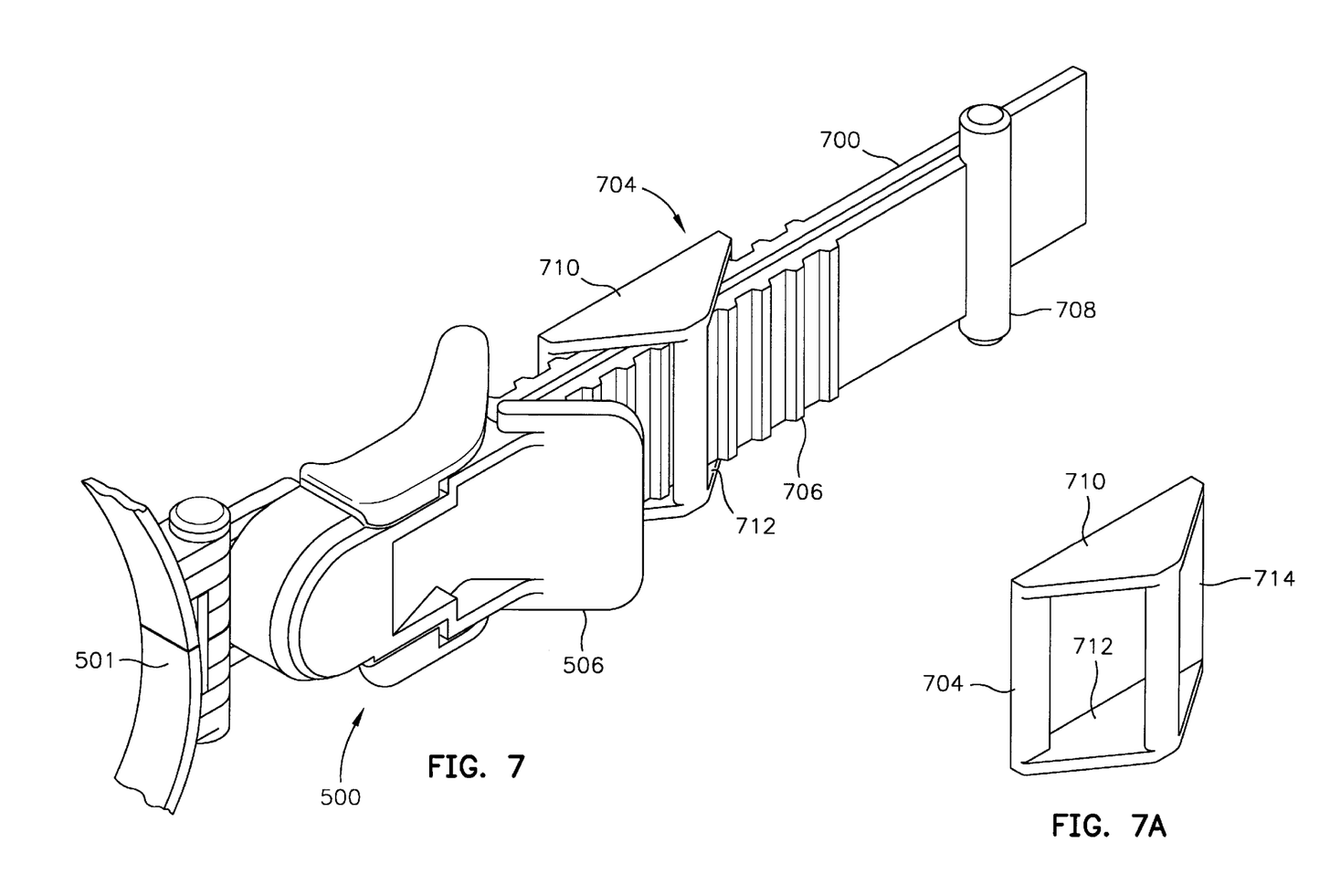
FIG. 7 is a perspective view of a preferred embodiment of the strap used in conjunction with the attachment device of FIG. 6.
FIG. 7A is a detail of a retainer clip employed with the strap of FIG. 7.

Preferably, the goggles are secured to the face of the wearer by placing a strap around the head of the goggles wearer. However, the strap may be placed around a hat worn by the goggle wearer. In either case, the strap, shown in FIG. 7, is attached to the bezel 302 of the goggles. However, removably or permanently attaching the strap directly to the frame 202 would also be acceptable. The strap may be flat or cylindrical, and is preferably molded from liquid silicone elastomers in the embodiment, but could also be constructed from rubber, plastic, fiber, or like materials. One end of the strap 700 cooperates with an attachment means, such as that shown in FIGS. 5A–5C, coupled to the first end 304 of the bezel 302. The other end of the strap cooperates with another attachment means which is attached to the second end 306 of the bezel.

Figure 5A:
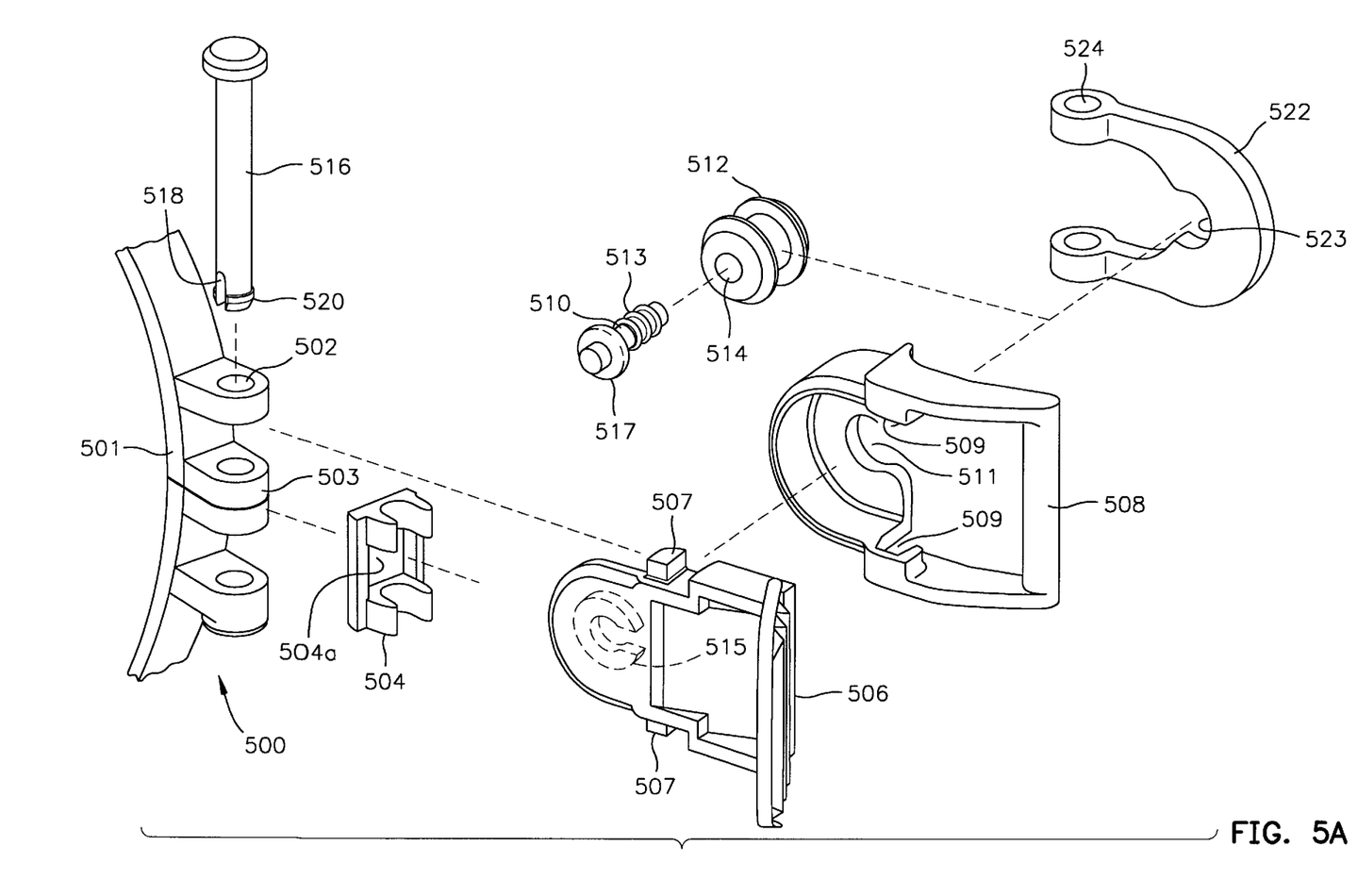
FIG. 5A is a perspective exploded view of the elements which, when assembled, constitute a preferred embodiment of an attachment device portion of the invention for the strap of the goggles of the invention.

A preferred attachment means for use with the strap in securing it to bezel 302 uses two attachment devices 500 shown in FIG. 5A. One strap attachment device 500 couples to the first end 304 of the bezel 302 and another such device couples to the second end 306 of the bezel.

Figure 5B:
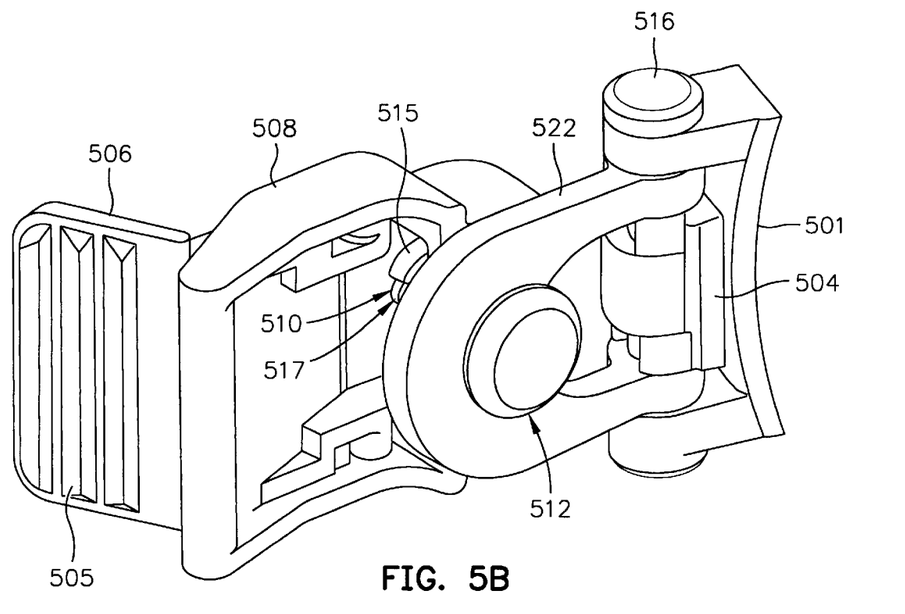
FIG. 5B is a perspective inside view of the assembled elements of the attachment device of FIG. 5A.
Figure 5C:
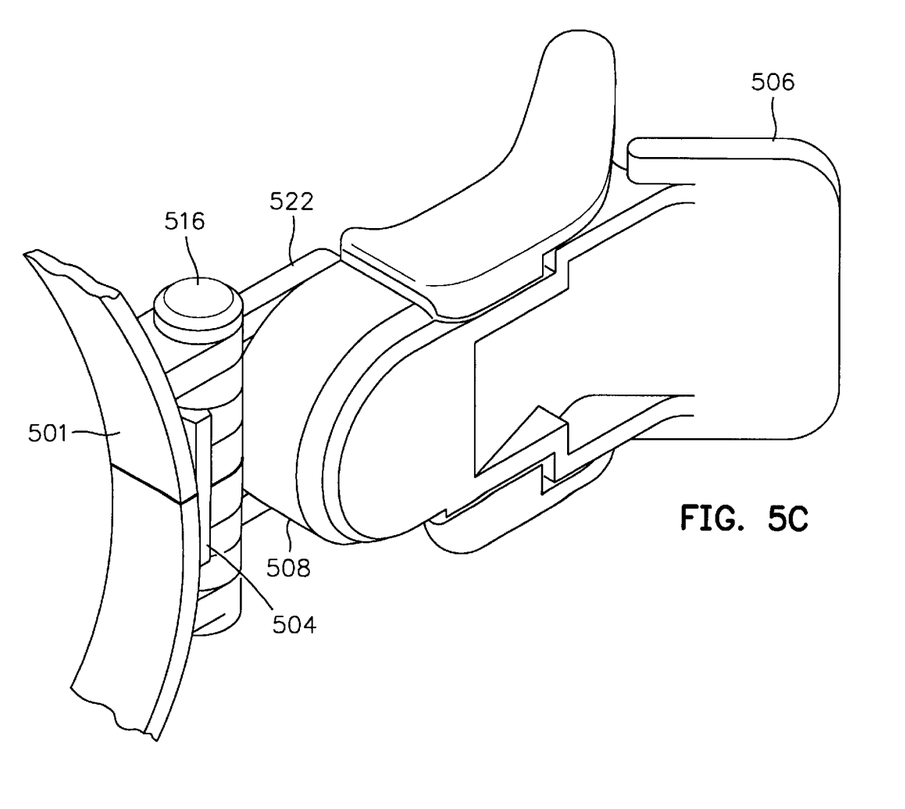
FIG. 5C is a perspective outside view of the assembled elements of the attachment device of FIG. 5A.

To fully appreciate integral attachment device 500, reference is made to FIGS. 5A–5C. FIG. 5A illustrates the elements of the attachment device connected to the bezel clip receiver 501 and including a bezel clip 504. The bezel clip receiver 501 has a plurality of receiver bores 502 which are substantially coaxial. The bezel clip 504 is removably snapped onto the bezel clip receiver 501 which is integral to the bezel as opening 504a receives the center projection 503. A ratchet pawl 506 having mounting protrusions 507 is also shown, as is a strap hanger 508 having first reliefs 509 and a second relief 511.

FIG. 5A also shows a pivot axle 512 having an axle bore 514. A pivot axle plug 510, having ridges 513, is inserted into the axle bore 514. The plug 510 may be a flexible elastomer plug that allows both compressive and tensile movement of the plug. The pivot axle plug 510 is sized and positioned so that the ridges 513 are removably held within the axle bore. A protruding portion 517 (shown in FIG. 5A) of the pivot axle plug 510 may protrude beyond one end of the pivot axle 512 when the pivot axle plug is fully inserted into the pivot axle.

The pivot axle 512 is rotatably coupled within the second relief 511 of the strap hanger 508, and the protruding portion 517 of the pivot axle plug 510 rotatably engages locking arms 515 (shown in FIG. 5A) of the ratchet pawl 506. The interlocking of locking arms 515 with the pivot axle 512 causes the mounting protrusions 507 to be securely held within the first reliefs 509 of the strap hanger 508. Mounting the ratchet pawl 506 in this fashion allows it to be cantilevered when a pressure is applied to ribs 505 (shown in FIG. 5B) in a direction substantially perpendicular to the surface from which the ribs extend, compressing the pivot axle plug 510.

FIG. 5B shows the assembled relationship of the pivot axle 512, the strap hanger 508, and the ratchet pawl 506. A pivot plate 522 is rotatably coupled with the pivot axle 512. This rotatable coupling occurs when plate relief 523 shown in FIG. 5A is slid into place around the pivot axle 512. Ridges 513 are used on the pivot axle plug 510 which is inserted into the axle bore 514 of the pivot axle 512, and the pivot axle allows the pivot plate 522 to be "snapped" into place around the pivot axle. The pivot plate 522 is rotatably coupled to the bezel clip receiver 501 by placing pivot plate bores 524 (shown in FIG. 5A) in axial alignment with the receiver bores 502.

A hinge pin 516 is used to rotatably couple the bezel clip receiver 501 with the pivot plate 522. Note that in FIG. 5B the ratchet pawl 506 is securely held within the strap hanger 508 by the interlocking cooperation of the protruding portion 517 of the pivot axle plug 510 and the locking arms 515 of the ratchet pawl. The pivot axle 512 serves to rotatably secure the strap hanger 508 to the pivot plate 522. In turn, the pivot plate 522 is rotatably coupled to the bezel clip receiver 501. The bezel clip 504 cradles the hinge pin 516. FIG. 5C shows a perspective view of the assembled device, further illustrating the relationship of the cooperating elements as shown in this embodiment.

Figure 6:
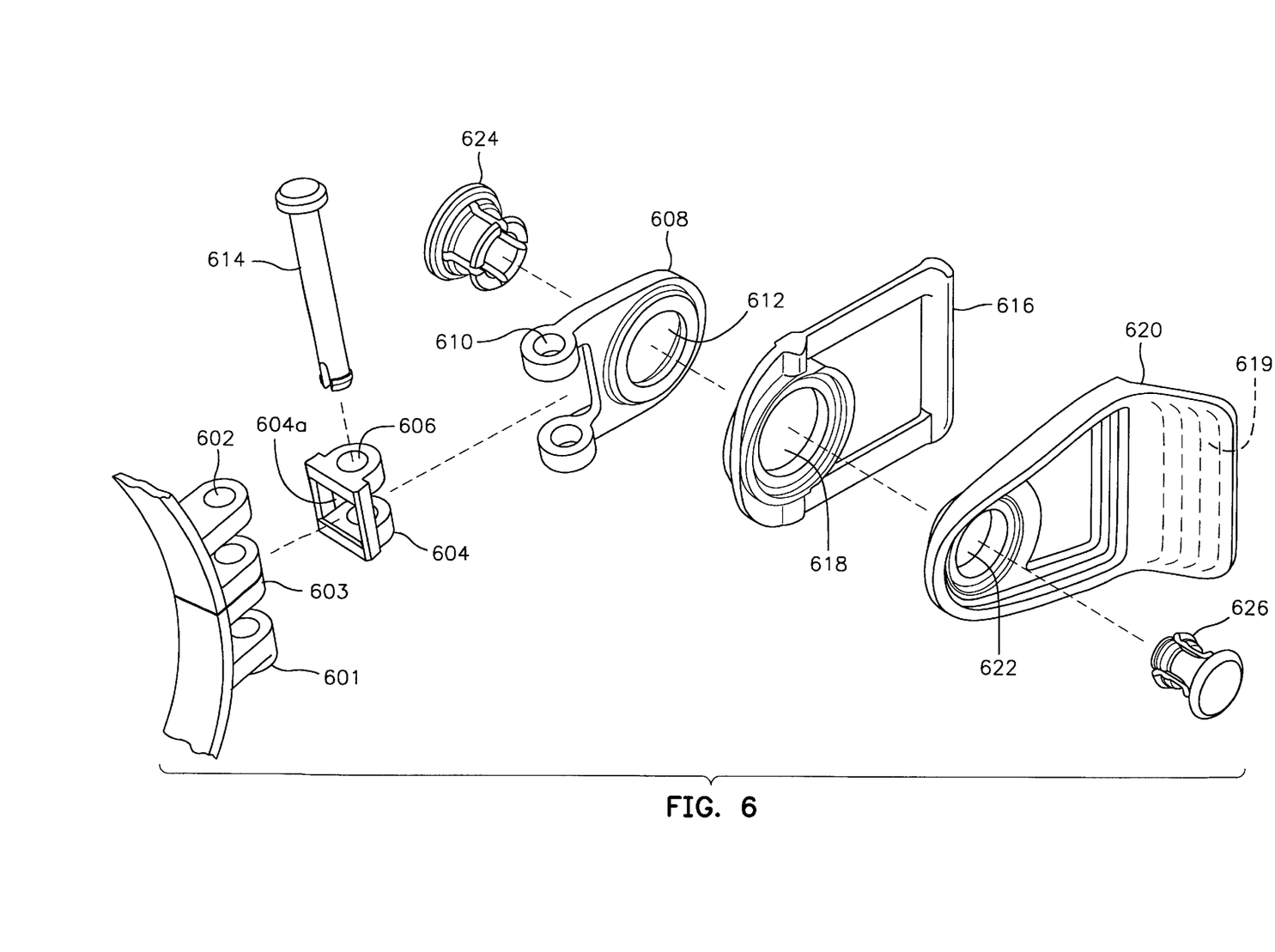
FIG. 6 is a perspective exploded view of an alternative embodiment of attachment device portion of the invention for the strap of the goggles of the invention.

An alternate embodiment 600 of the strap attachment device is shown in FIG. 6. A bezel clip receiver 601 having a plurality of receiver bores 602 is integral to one end of the bezel 302. Opening 604a of bezel clip 604 slides over protrusion 603 of the bezel clip receiver. A pivot mount 608 having a pivot bore 610 interlaces with the bezel clip 604 and the bezel clip receiver 601 so that receiver bores 602, the bezel clip bores 606, and the pivot bore 610 are all substantially coaxial when assembled. A hinge pin 614 engages receiver bores 602 of receiver 601, the bezel clip bores 606, and the pivot bores 610 so that the hinge pin and bores cooperate and allow for rotational displacement of the pivot mount 608. The pivot mount has a mounting bore 612 which cooperates with a strap hanger bore 618, which is integral to a strap hanger 616, and a ratchet pawl bore 622 which is integral to a ratchet pawl 620, to allow the strap to be adjusted when the goggles are fitted to the head of the wearer. The pivot mount mounting bore 612, strap hanger bore 618 and ratchet pawl bore 622 are interconnected by a removable pivot pin 624 which cooperates with a pivot retainer 626 which is removably connected thereto. Winged ribs 619 are formed on one side of the ratchet pawl 620 to allow easier displacement of the ratchet pawl.

A perspective view of one end of the strap 700 engaged by the attachment device 500, as shown in FIGS. 5A–5C, is illustrated in FIG. 7. As discussed above, each end of the strap engages a respective attachment device 500. However, FIG. 7 only shows one end of the strap engaging one version of an attachment device for clarity purposes. Ribs 706 are integral to the strap in one preferred embodiment and assist the strap 700 in being captured by the attachment device and in preventing unwanted adjustment of the goggles when they are worn by the user. The ratchet pawl 506 is shown in its resting position after engagement of the strap. Compression of the pivot axle plug 510 (FIG. 5A) provides the force to keep the ratchet pawl 506 in contact with the strap 700. A bar 708, integral to the strap 700, is shown in its preferred position relative to one end of the strap. This bar is intended to prevent the end of the strap from inadvertently disengaging from the attachment device 500 when the goggles are adjusted for fit by the wearer. A bar 708 is placed similarly to that shown at each end of the strap. Although it is preferred that the bar 708 be integral to the strap, the bar may be a separate device which is coupled to the strap and performs the same anti-disengagement function.

The typical retainer clip 704 which is used in conjunction with the strap is shown in FIGS. 7 and 7A. This retainer clip has a first side element 710 and a second side element 712. These side elements are interconnected in such a way that the strap 700 is permitted to pass between them, and allows for any loose end (,f the strap to be captured by the retainer clip. A side connector such as bars 714 would suffice for this interconnection as would any other suitably configured side connecting element.

In one embodiment, the invention described above is designed to meet the needs of a person who requires eye protection in ultra-hazardous conditions, and is specifically designed to meet the needs of a firefighter. The goggles are placed over the eyes of the firefighter, preferably prior to entering a hazardous condition. The frame 202 is specifically designed to fit over the spectacles, if any, of a firefighter without necessitating the removal of the spectacles when the goggles are either placed over the eyes or are removed from over the eyes of the firefighter. In the preferred embodiment, as shown in FIG. 1, the frame is also designed so that the goggle may be used in conjunction with a breathing device such as a respirator. In another embodiment, the nose cover 308 of the bezel 302 can be used to protect the nose of the wearer.

The goggles described above, in the preferred embodiment, are constructed of heat-resistant materials which may withstand minimum temperatures of about 550° F. for a minimum of five minutes without deforming. The first and second openings 217 and 226 allow indirect venting of the goggles and prevent fogging of the lens while allowing drainage of perspiration that might otherwise be trapped between the face of the wearer and the lens. Dams 215 which surround the openings 217 and 226 cooperate with opening covers 310 in order to prevent external materials from contacting the eyes of the wearer.

The unique design of the goggles frame eliminates interference with spectacles and allows the goggles to be placed over the eyes of the wearer and to be removed without the removal of the spectacles. The lens 400, as shown in one embodiment is canted within the frame in order to increase the lower peripheral vision of the wearer and allow the wearer to see the ground immediately before him. The cant referred to can be easily seen by referencing the side view of the frame 220 shown in FIG. 2D. In one embodiment of the present invention, the cant angle is about 12 degrees. Because the preferred embodiment is designed for firefighters, and because firefighters are customarily in areas where the footing is unstable and hazardous, increased lower peripheral vision is important. Preferably, the lens is injection molded and optically corrected to eliminate distortion at the inner face of the multiple optical zones.

Although the goggles have been described in considerable detail with reference to certain preferred versions thereof, other versions are possible. For example, in an alternate embodiment, the frame 202 may be strapped around or attached to the head gear of the goggles wearer. By attaching the goggles to the headgear of the wearer, the goggles may be securely held over the eyes of the wearer and removed by removing the helmet. Because other versions are anticipated, the spirit and scope of the appended claims should not be limited to description of the preferred versions contained herein. It is likely that improvements and modifications will occur to those who are skilled in this art which are within the spirit and scope of the accompanying claims.

What is claimed is:

1. A pair of goggles for protecting the eyes of a wearer, comprising:

a frame for sealing substantially completely against the face of the wearer;

a curvilinear lens with a center substantially centered in said frame, said lens comprising:

an inner surface;

an outer surface, wherein said outer surface diverges with said inner surface so that a thickness of said lens as measured between said inner surface and said outer surface is maximized toward said center of said lens;

a lens perimeter;

tabs extending from said perimeter and directed substantially perpendicular to said outer surface; and multiple optical zones integral to said lens, said multiple optical zones comprising:

a central optical zone positioned at said center of said lens; and side optical zones on either side of and spaced by said central optical zone, said side optical zones comprising:

a first side optical zone contiguous to said central optical zone;

a second side optical zone contiguous to said central optical zone; and rear optical zones spaced from said central optical zone by said side optical zones, said rear optical zones comprising:

a first rear optical zone contiguous to said first side optical zone; and a second rear optical zone contiguous to said second side optical zone;

a lens retention means cooperating with said tabs and said frame to removeably couple said lens to said frame;

a strap coupled to said goggles for securing said goggles to the wearer; and a strap attachment means for adjustably securing said strap to said goggles.

2. The goggles recited in claim 1, wherein the goggles further comprise:

a bezel to assist in securing said lens to said goggles and said goggles to said wearer, the bezel including a first end and a second end; and a bezel attachment means for securing said bezel to said frame.

3. The goggles recited in claim 2, wherein said bezel further includes slots to engage said tabs extending from said lens' said perimeter.

4. The goggles recited in claim 3, wherein said strap attachment means comprises a plurality of attachment devices, each attachment device comprising:

a bezel clip receiver coupled to one end of said bezel and including a receiver bore;

a bezel clip formed with a bore and coupled to said bezel clip receiver;

a pivot mount having a pivot bore, and including at least one pivot mount mounting bore for coupling said pivot mount with said bezel clip;

a hinge pin for pivotly attaching said pivot mount to said bezel clip, wherein said hinge pin passes through said bezel clip bore and at least one pivot mount mounting bore;

a strap hanger having a bore;

a ratchet pawl having a bore;

a pivot pin wherein said pivot pin passes through said strap hanger bore and said ratchet pawl bore; and a pivot pin retainer which cooperates with said pivot pin to pivotly and rotatably secure said strap hanger and said ratchet pawl to said pivot mount, wherein said strap hanger is located between said ratchet pawl and said pivot mount.

5. The goggles recited in claim 3, wherein said bezel attachment means comprises a plurality of attachment devices, each strap attachment device comprising:

a bezel clip receiver coupled to one end of said bezel and including at least one bezel clip receiver bore;

a bezel clip formed with cradles and coupled to said bezel clip receiver;

a ratchet pawl formed with a plurality of mounting protrusions and a ratchet pawl cradle for receiving a pivot axle plug to secure said ratchet pawl to said pivot axle plug having a plurality of ridges which encircle said pivot axle plug;

a strap hanger formed with a plurality of first reliefs for rotatably engaging said mounting protrusions on said ratchet pawl, a second relief for rotatably engaging a pivot axle having an axis and an axle bore, wherein said axle bore is positioned substantially coaxial to said axis of said pivot axle and said pivot axle plug inserts into said axle bore;

a pivot plate including a plurality of pivot plate bores and a pivot plate relief, wherein said pivot plate relief cooperates with said pivot axle to rotatably secure said pivot axle at a location substantially opposite to said ratchet pawl; and a hinge pin, wherein said hinge pin is inserted through said bezel clip receiver bore, each of said pivot plate bores, and is partially captured by said bezel clip cradles, whereby said hinge pin rotatably secures said pivot plate to said bezel clip receiver.

6. The goggles recited in claim 3, wherein said frame further comprises:

a flange side;

a lens side opposite said flange side;

an upper side;

a lower side opposite said upper side;

a first strap end;

a second strap end, wherein said first strap end is opposite to said second strap end;

a nose section integral to said lower side and adapted to seal said nose section atop the wearer's nose; and a curved flexible face flange coupled to said flange side, wherein said curved flexible face flange is interrupted by said nose section and is adapted to seal against the face of the wearer.

7. The goggles recited in claim 6, wherein said frame further comprises:

a first gutter formed into said frame and juxtaposed to said curved flexible face flange;

a second gutter formed into said frame and juxtaposed to said lens perimeter;

first openings molded into said frame on said upper side between said lens side and said flange side, and juxtaposed to said second gutter;

second openings molded into said frame on said lower side between said lens side and said flange side, and juxtaposed to said second gutter;

a plurality of dams coupled to said frame and surrounding said first and said second openings; and channels formed into each of said first and second strap ends and running between said second gutter and said flange side, wherein said channels bifurcate said curved face flange and said first gutter.

8. The goggles recited in claim 1, wherein the goggles further comprise:

a strap for securing said goggles, wherein said strap has two ends and a top and a bottom surface, said strap comprising:

an array of ribs spaced apart and protruding from at least one of said top or bottom surfaces;

at least one bar on each of said ends of said strap whereby said bars prevent said strap from becoming disengaged from said strap attachment means; and a strap retainer means adjustably attached to said strap whereby any unrestrained end of said strap may be captured.

9. The goggles recited in claim 3, wherein said bezel incorporates a nose shield sized and positioned so that the nose of the wearer of the goggles is covered by said nose shield when the goggles are fitted to the wearer's face.

10. The goggles recited in claim 3, wherein said lens retention means comprises a lens retention channel integral to said frame and adapted for capturing and securing said lens around said lens perimeter.

11. The goggles recited in claim 10, wherein said lens retention channel is cradled within said bezel attachment means, said bezel attachment means comprising a bezel attachment channel integral to said bezel for capturing and securing said lens retention channel located within a lens surround area, and wherein said lens retention channel is located between said lens perimeter and said bezel attachment channel.

12. The goggles recited in claim 1, wherein said lens is canted within the goggles to increase the goggles visibility range.

13. The goggles recited in claim 12, wherein said cant angle is about 12 degrees.

14. The goggles recited in claim 10, further comprising a T-shaped lip integral to said lens perimeter wherein said lens retention channel is T-shaped and located to cooperate with said T-shaped lip integral to said lens perimeter to capture and removably secure said lens.

15. The goggles recited in claim 13, wherein said T-shaped lip extends substantially along said lens perimeter where said lens perimeter is adjacent to said upper side of said frame wherein said frame comprises a curved one piece molded flexible frame, and wherein said T-shaped lip extends substantially along said lens perimeter where said lens perimeter is adjacent to said lower side of said frame.

16. The goggles recited in claim 15, wherein said T-shaped lip is centrally bifurcated where it extends along said lens perimeter where said lens perimeter is adjacent to said upper side of said frame.

17. The goggles recited in claim 8, wherein said strap retainer means comprises at least one retainer clip suitable for capturing any unrestrained end of said strap after said goggles are adjusted to fit the head of the wearer.

18. The goggles recited in claim 8, wherein said strap retainer means comprises:
   a first side element including an elongated base;
   a second side element including an elongated base; and
   a means for interconnecting said first and second side elements in such a manner as to allow said strap and strap ends to be adjustably captured therebetween.

19. The goggles recited in claim 3, said bezel further comprising:
   opening covers coupled to said bezel wherein said opening covers cooperate with a plurality of dams to shield said first and second openings;
   said frame further comprising:
      a plurality of holes adjacent to said first openings;
      a plurality of barbed fasteners integral to said opening covers that shield said first openings, wherein said plurality of barbed fasteners button into said holes adjacent to said first openings to prevent a gap from opening up between said frame and said first opening covers.

20. The goggles recited in claim 5, wherein said goggles are constructed of materials capable of withstanding heat of up to about 550 degrees Fahrenheit for at least five minutes without deforming.

21. A lens comprising:
   a curved inner surface;
   a curved outer surface;
   a lens perimeter;
   at least one central optical zone;
   at least one side optical zone;
   at least one rear optical zone; and
   wherein each optical zone has a unique curvature; and
   wherein said optical zones comprise:
      said at least one central optical zone is positioned at the center of said lens wherein said curved outer surface diverges with said curved inner surface about said central optical zone so that a thickness between said curved inner surface and said curved outer surface is maximized toward said center of said central optical zone;
      said at least one side optical zone having a curvature and separated by said at least one central optical zone, said at least one side optical zone comprising:
         a first side optical zone contiguous to said at least one central optical zone;
         a second side optical zone contiguous to said at least one central optical zone; and
      said at least one rear optical zone spaced from said at least one central optical zone by said side optical zones, said at least one rear optical zone comprising:
         a first rear optical zone contiguous to said first side optical zone, wherein said curvature of said first side optical zone is equal to a curvature of said first rear optical zone at said contiguous location; and
         a second rear optical zone contiguous to said second side optical zone, wherein said curvature of said second side optical zone is equal to a curvature of said second rear optical zone at said contiguous location.

22. The lens recited in claim 21, wherein a T-shaped lip is integral to said lens perimeter.

23. A pair of goggles comprising:
   a curved one piece molded flexible frame including a flange side opposite a lens side, an upper side opposite a lower side, a first strap end, and a second strap end, wherein said first strap end is opposite to said second strap end, said curved one piece molded flexible frame comprising:
   a nose section integral to said lower side and adapted to seal said nose section atop the wearer's nose;
   at least one nose section relief incorporated into said nose section;
   a curved face flange molded into said flange side, wherein said curved face flange is interrupted by said nose section and is adapted to seal against the face of the wearer;
   a curved lens surround area molded into said lens side;
   a lens retention means integral to said lens surround area;
   a first gutter molded into said one piece molded flexible frame and juxtaposed to said curved face flange;
   a second gutter molded into said one piece molded flexible frame, wherein said second gutter is juxtaposed to said lens surround area;
   first openings molded into said one piece molded flexible frame on said upper side between said lens side and said flange side, and juxtaposed to said second gutter;
   a plurality of holes adjacent to said first openings;
   second openings molded into said one piece molded flexible frame on said lower side between said lens side and said flange side, and juxtaposed to said second gutter;
   a plurality of dams formed into said one piece molded flexible frame and surrounding said first and said second openings;
   channels formed into each of said first and second strap ends and running between said second gutter and said flange side, wherein said channels bifurcate said curved face flange and said first gutter;

a curvilinear lens including a curved inner surface, a curved outer surface, a lens perimeter including tabs extending therefrom and directed substantially perpendicular to said outer surface, said tabs cooperating with said lens retention means to prevent the lens and frame from separating, and multiple optical zones integral thereto, said multiple optical zones comprising:
  a curvilinear central optical zone centrally positioned within said lens and including a centerline centrally located within said central optical zone and extending between said upper side and said lower side of said curved one piece molded flexible frame, wherein said curved outer surface converges with said curved inner surface so that the distance between said curved inner surface and said curved outer surface is maximized towards the centerline of said central optical zone and decreases horizontally across said central optical zone;
  curvilinear side optical zones wherein said side optical zones each have a vertex and at least one radius of curvature and are separated by said central optical zone, said side optical zones comprising:
    a first side optical zone contiguous to said central optical zone;
    a second side optical zone contiguous to said central optical zone;
    rear optical zones wherein said rear optical zones are separated by said central optical zone and said side optical zones, said rear optical zones comprising:
      a first rear optical zone abutting and contiguous to said first side optical zone, wherein said radius of curvature of said first side optical zone is equal to the radius of curvature of said first rear optical zone at said abutting location;
      a second rear optical zone abutting and contiguous to said second side optical zone, wherein said radius of curvature said second side optical zone is equal to the radius of curvature of said second rear optical zone at said abutting location;
a strap for securing said goggles over the eyes of the wearer, wherein said strap has two ends, and a top and bottom surface, said strap comprising:
  an array of parallel ribs spaced apart and protruding from at least one of said top or bottom surfaces; and
  at least one integral bar on each of said ends of said strap, whereby said integral bars prevent said strap from becoming disengaged from said attachment means;
  a strap retainer means adjustably attached to said strap, whereby any unrestrained end of said strap may be captured;
an attachment means for securing said strap to said goggles;
a curved molded bezel including a first end and a second end, said bezel comprising:
  bezel attachment means for securing said bezel to said curved lens surround area;
  opening covers integral to said curved molded bezel wherein said opening covers cooperate with said plurality of dams to shield said first and second openings;
  slots in said bezel for engaging said tabs extending from said lens perimeter; and
  a plurality of barbed fasteners integral to said opening covers that shield said first openings molded into said upper side of said one piece molded flexible frame, wherein said plurality of barbed fasteners button into said holes adjacent to said first openings to prevent a gap from opening up between said one piece molded flexible frame and said first opening covers when the one piece molded flexible frame is flexed;
wherein said goggles are constructed of materials capable of withstanding heat of up to about 550 degrees Fahrenheit for at least five minutes without deforming.

24. The goggles recited in claim 23, wherein said lens retention means comprises a lens retention channel integral to said curved lens surround area and adapted for capturing and securing said lens around said lens perimeter.

25. The goggles recited in claim 24, wherein said curvilinear lens is canted within said goggles.

26. The goggles as recited in claim 25, and further comprising a T-shaped lip integral to said lens perimeter wherein said lens retention channel is T-shaped and located to cooperate with said T-shaped lip integral to said lens perimeter to capture and removably secure said lens.

27. The goggles as recited in claim 26, wherein said T-shaped lip extends substantially along said lens perimeter where said lens perimeter is adjacent to said upper side of said curved one piece molded flexible frame, and wherein said T-shaped lip extends substantially along said lens perimeter where said lens perimeter is adjacent to said lower side of said curved one piece molded flexible frame.

28. The goggles as recited in claim 27, wherein said T-shaped lip is centrally bifurcated where it extends along said lens perimeter where said lens perimeter is adjacent to said upper side of said curved one piece molded flexible frame.

29. The goggles recited in claim 28, wherein said cant angle is about 12 degrees.

30. The goggles recited in claim 29, wherein said lens retention channel is securely cradled within said bezel attachment means, said bezel attachment means comprising a bezel attachment channel integral to said bezel for capturing and securing said curved lens surround area, and wherein said lens retention channel is located between said lens perimeter and said bezel attachment channel.

31. The goggles recited in claim 30, wherein said strap retainer means comprises at least one retainer clip suitable for capturing any unrestrained end of said strap after said goggles are adjusted to fit the head of the wearer.

32. The goggles recited in claim 31, wherein said strap retainer means comprises:
  a first side element including an elongated base;
  a second side element including an elongated base; and
  a means for interconnecting said first and second side elements in such a manner as to allow said strap and strap ends to be adjustably captured therebetween.

33. The goggles recited in claim 32, wherein said attachment means comprises a plurality of attachment devices, each attachment device comprising:
  a bezel clip receiver coupled to one end of said bezel and including at least one bezel clip receiver bore;
  a bezel clip including bezel clip cradles and coupled to said bezel clip receiver;
  a pivot axle having an axis and an axle bore, wherein said axle bore is positioned substantially coaxial to said axis of said pivot axle;
  a pivot axle plug having a plurality of ridges which encircle said pivot axle plug, wherein said pivot axle plug inserts into said axle bore;

a ratchet pawl including a plurality of mounting protrusions and including a ratchet pawl cradle for securing said ratchet pawl to said pivot axle plug;

a strap hanger including a plurality of first reliefs for rotatably engaging said mounting protrusions on said ratchet pawl, and including a second relief for rotatably engaging a pivot axle;

a pivot plate including a plurality of pivot plate bores and a pivot plate relief, wherein said pivot plate relief cooperates with said pivot axle to rotatably secure said pivot plate to said pivot axle at a location substantially opposite to said ratchet pawl; and a hinge pin, wherein said hinge pin is inserted through said bezel clip receiver bore, each of said pivot plate bores, and is partially captured by said bezel clip cradles, whereby said hinge pin rotatably secures said pivot plate to said bezel clip receiver.

34. The goggles recited in claim 32, wherein said attachment means comprises a plurality of attachment devices, each attachment device comprising:

a bezel clip receiver coupled to one of said ends of said bezel and including a receiver bore;

a bezel clip including a bezel clip bore and coupled to said bezel clip receiver;

a pivot mount having a pivot bore, and including at least one pivot mount mounting bore for coupling said pivot mount with said bezel clip;

a hinge pin for pivotly attaching said pivot mount to said bezel clip, wherein said hinge pin passes through said bezel clip bore and at least one pivot mount mounting bore;

a strap hanger having a strap hanger bore;

a ratchet pawl having a ratchet pawl bore;

a pivot pin wherein said pivot pin passes through said strap hanger bore and said ratchet pawl bore; and a pivot pin retainer which cooperates with said pivot pin to pivotly and rotatably secure said strap hanger and said ratchet pawl to said pivot mount, wherein said strap hanger is located between said ratchet pawl and said pivot mount.

35. The goggles recited in claim 23, wherein said distance between said curved inner surface and said curved outer surface is substantially between 0.08 inch to 0.100 inch.

36. The goggles recited in claim 24, where a foam seal cooperates with said curved face flange to seal the goggles against the face of the wearer.

37. A pair of goggles for protecting the eyes of an individual, the pair of goggles comprising:

a frame adapted to seal against a face of the individual, the frame configured to allow the individual to wear a pair of spectacles underneath the pair of goggles; and a lens coupled to the frame, the lens comprised of a plurality of optical zones, the plurality of optical zones shaped to minimize any distortion of objects viewed selectively though any of the optical zones;

wherein the plurality of optical zones are hyperbolically curved in a direction substantially perpendicular to a vertical centerline passing through a center of the lens.

38. A pair of goggles comprising:

a frame adapted to seal substantially completely against a face of an individual, the frame comprising at least one vent;

a lens comprising at least two optical zones, wherein each optical zone has a unique curvature; and a bezel configured to removeably couple the lens to the frame, the bezel covering at least a portion of the vent.

39. The goggles according to claim 38, wherein:

the lens is curvilinear and the lens has an outer surface the diverges from an inner surface so that a thickness of the lens as measured between the inner surface and the outer surface is maximized toward a center of the lens thereby minimizing distortion of objects viewed through the lens.

40. The goggles according to claim 38, and further including:

at least one tab extending from a lens perimeter, the tab directed substantially perpendicular to a lens outer surface, the tab removeably coupling the lens to the frame.

41. The goggles according to claim 38, further including:

a strap coupled to the pair of goggles for securing the pair of goggles to the individual; and a strap attachment means for adjustably securing the strap to the pair of goggles.

42. The goggles according to claim 38, wherein the lens is comprised of a plurality of optical zones, the plurality of optical zones shaped to minimize any distortion of objects viewed selectively though any of the optical zones.

43. The goggles according to claim 42, wherein the plurality of optical zones comprise:

a central optical zone positioned about a center of the lens;

side optical zones on either side of the central optical zone;

rear optical zones adjacent to the side optical zones; and wherein distortion of objects selectively viewed through the central, side and rear optical zones is minimized.

44. The goggles according to claim 42, wherein the plurality of optical zones are hyperbolically curved in a direction substantially perpendicular to a vertical centerline passing through a center of the lens.

45. The goggles according to claim 42, wherein a radius of curvature of each of the plurality of optical zones is equal where each of the plurality of optical zones borders each other.

46. The goggles according to claim 38, wherein the lens is canted to maximize a lower peripheral vision of the individual.

47. The goggles according to claim 38, and further including at least one gutter located on the frame, the gutter configured to channel liquids away from the face of the individual.

* * * * *